United States Patent
Coates et al.

(10) Patent No.: US 8,658,638 B2
(45) Date of Patent: Feb. 25, 2014

(54) MINERALOCORTICOID RECEPTOR ANTAGONIST AND METHODS OF USE

(75) Inventors: David Andrew Coates, Indianapolis, IN (US); Konstantinos Gavardinas, Monrovia, IN (US); Prabhakar Kondaji Jadhav, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 94 days.

(21) Appl. No.: 13/203,518

(22) PCT Filed: Mar. 4, 2010

(86) PCT No.: PCT/US2010/026138
§ 371 (c)(1),
(2), (4) Date: Aug. 26, 2011

(87) PCT Pub. No.: WO2010/104721
PCT Pub. Date: Sep. 16, 2010

(65) Prior Publication Data
US 2011/0312954 A1 Dec. 22, 2011

Related U.S. Application Data

(60) Provisional application No. 61/159,578, filed on Mar. 12, 2009.

(51) Int. Cl.
*C07D 498/04* (2006.01)
*A61K 31/5365* (2006.01)

(52) U.S. Cl.
USPC .................................... 514/230.5; 544/105

(58) Field of Classification Search
USPC ..................................... 544/105; 514/230.5
See application file for complete search history.

(56) References Cited

FOREIGN PATENT DOCUMENTS

| WO | 2004052847 | 6/2004 |
|----|------------|--------|
| WO | 2005066161 | 7/2005 |
| WO | 2009085584 | 7/2009 |

*Primary Examiner* — Kahsay Habte
(74) *Attorney, Agent, or Firm* — Elizabeth Dingess-Hammond; Alexander Wilson

(57) ABSTRACT

The present invention provides a compound of the formula:

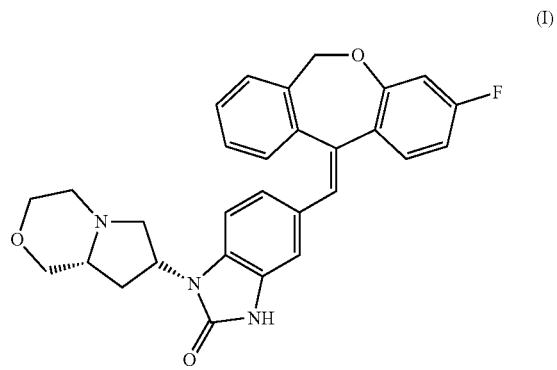

(I)

or a pharmaceutically acceptable salt thereof; pharmaceutical compositions comprising Compound (I) in combination with a suitable carrier, diluent, or excipient; and methods for treating physiological disorders, particularly congestive heart failure, hypertension, diabetic nephropathy, or chronic kidney disease, comprising administering Compound (I), or a pharmaceutically acceptable salt thereof.

7 Claims, No Drawings

MINERALOCORTICOID RECEPTOR ANTAGONIST AND METHODS OF USE

This application is a 371 of PCT/US2010/026138, filed Mar. 4, 2010, which claims the benefit of U.S. Provisional Application Ser. No. 61/159,578 filed Mar. 12, 2009.

The present invention relates to tricyclic compounds that are useful as therapeutic agents, to pharmaceutical compositions comprising the compounds, to methods of using the compounds to treat physiological disorders in patients, and to intermediates and processes useful in the synthesis of the compounds.

Aldosterone, the primary endogenous mineralocorticoid, promotes sodium and water reabsorption and potassium excretion following interaction with the mineralocorticoid receptor (MR). Because of aldosterone's role in maintaining electrolyte and water balance, MR antagonists have been used for the treatment of numerous physiological disorders including hypertension, hypokalemia, myocardial arrhythmias, Bartter's Syndrome, as well as disorders of primary or secondary hyperaldosteronism such as Conn's Syndrome. More recently, MR antagonists have been used in the treatment of congestive heart failure and acute myocardial infarction. In addition, MR antagonists have also proven effective in preclinical models of kidney disease and in combination with standard therapy to reduce proteinuria in patients suffering from renal disorders such as chronic kidney disease including diabetic nephropathy.

However, existing steroidal MR antagonists produce concomitant effects which limit their safety and/or effectiveness. For example, spironolactone is nonselective and cross reacts with other nuclear hormone receptors (e.g. the androgen receptor (AR), the progesterone receptor (PR), or the glucocorticoid receptor (GR)) which mediate other physiological processes. Spironolactone therapy has also been associated with hyperkalemia as well as gynecomastia, erectile dysfunction, reduced libido, irregular menses, as well as gastric distress. Eplerenone, though selective for MR relative to the other nuclear hormone receptors, has also been associated with hyperkalemia. Thus, there remains a need in the art for alternatives to current MR antagonist therapy.

The object of the present invention is to provide a nonsteroidal MR ligand which possesses MR antagonist activity. More particularly, it is an object to provide a nonsteroidal MR antagonist which binds to MR with greater affinity relative to AR, PR, and GR. As a more particular embodiment, it is an object of the present invention to provide a nonsteroidal MR antagonist which binds to MR with greater affinity relative to AR, PR, and GR, and which possesses potent reno- or cardio-protective activity. As an even more particular embodiment, it is an object to provide a nonsteroidal MR antagonist which binds to MR with greater affinity relative to AR, PR, and GR, and which posseses potent reno- or cardio-protective activity, but with a reduced incidence or likelihood of producing hyperkalemia.

Tricyclic MR ligands are known in the art. For example WO 04/052847 and WO 05/066161 disclose tricyclic steroid hormone receptor modulators which are useful for treating disorders susceptible to mineralocorticoid receptor or glucocorticoid receptor modulation. The present invention relates to a particular dibenzooxepine, as given by Compound (I) below, which has a profile of in vitro and in vivo activity which indicates that it has utility in the treatment or prevention of disorders responsive to mineralocorticoid receptor antagonist therapy.

Accordingly, the present invention provides a compound of the formula

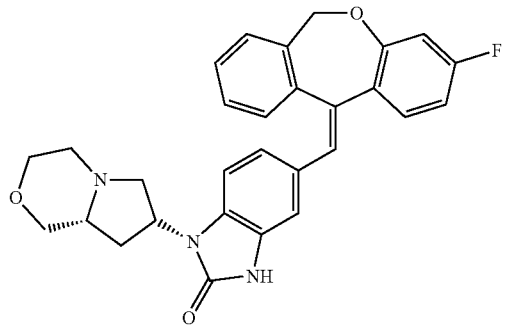

Compound (I)

(5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one)
or a pharmaceutically acceptable salt thereof.

As a particular embodiment, the present invention provides Compound (I), or a pharmaceutically acceptable salt thereof in crystalline form.

In another embodiment, the present invention provides a method of treating or preventing congestive heart failure, diabetic nephropathy, chronic kidney disease, hypertension, hypokalemia, myocardial arrhythmia, Bartter's Syndrome, primary or secondary hyperaldosteronism, or Conn's Syndrome, comprising administering to a patient in need thereof an effective amount of Compound (I), or a pharmaceutically acceptable salt thereof. As a more particular aspect, the present invention provides a method for treating or preventing congestive heart failure, hypertension, diabetic nephropathy, or chronic kidney disease comprising administering to a patient in need thereof an effective amount of Compound (I), or a pharmaceutically acceptable salt thereof.

The present invention also provides Compound (I), or a pharmaceutically acceptable salt thereof, for use in therapy. Further, the present invention provides Compound (I), or a pharmaceutically acceptable salt thereof, for use in the treatment or prevention of congestive heart failure, diabetic nephropathy, chronic kidney disease, hypertension, hypokalemia, myocardial arrhythmia, Bartter's Syndrome, primary or secondary hyperaldosteronism, or Conn's Syndrome. More particularly, the invention provides Compound (I), or a pharmaceutically acceptable salt thereof, for use in the treatment or prevention of congestive heart failure, hypertension, diabetic nephropathy, or chronic kidney disease.

In another embodiment, the present invention provides the use of Compound (I), or a pharmaceutically acceptable salt thereof for the manufacture of a medicament for the treatment or prevention of congestive heart failure, diabetic nephropathy, chronic kidney disease, hypertension, hypokalemia, myocardial arrhythmia, Bartter's Syndrome, primary or secondary hyperaldosteronism, or Conn's Syndrome. More particularly, the present invention provides the use of Compound (I), or a pharmaceutically acceptable salt thereof for the manufacture of a medicament for the treatment or prevention of congestive heart failure, hypertension, diabetic nephropathy, or chronic kidney disease.

In addition, the present invention provides a pharmaceutical composition comprising Compound (I), or a pharmaceutically acceptable salt thereof, in combination with one or more pharmaceutically acceptable carriers, diluents, or excipients. More particularly, the present invention provides a pharmaceutical composition for the treatment or prevention of congestive heart failure, hypertension, diabetic nephropathy, or chronic kidney disease, comprising Compound (I), or a pharmaceutically acceptable salt thereof, in combination with one or more pharmaceutically acceptable carriers, diluents or excipients. The present invention also encompasses novel intermediates and processes useful for the synthesis of Compound (I).

The present invention relates to pharmaceutically acceptable salts of Compound (I) as well as solvates of Compound (I), or pharmaceutically acceptable salts thereof. As such, when used herein, the term "Compound (I)" includes within its meaning any solvate of the compound. Examples of pharmaceutically acceptable salts and methods for their preparation are well within the knowledge of those skilled in the art. See for example, Stahl et al., "Handbook of Pharmaceutical Salts: Properties, Selection and Use," VCHA/Wiley-VCH, (2002); Gould, P. L., "Salt selection for basic drugs," *International Journal of Pharmaceutics*, 33: 201-217 (1986); and Bastin et al. "Salt Selection and Optimization Procedures for Pharmaceutical New Chemical Entities," *Organic Process Research and Development*, 4: 427-435 (2000). Particular mention is made of the tosylate salt of Compound (I), however, it is to be understood that the free base of Compound (I) is preferred.

The terms "R" and "S" are used herein as commonly used in organic chemistry to denote specific configurations of a chiral center. The terms "(±)", "R/S" or "R/S" refer to a racemic configuration of a chiral center. A partial list of priorities and a discussion of stereochemistry is contained in "Nomenclature of Organic Compounds: Principles and Practice", (J. H. Fletcher, et al., eds., 1974). As used herein, the designation "—" refers to a bond that protrudes forward out of the plane of the page, whereas the designation "⋯⋯" refers to a bond that protrudes backward out of the plane of the page.

As will be appreciated by one of ordinary skill in the art, molecules containing a carbon-carbon or carbon-nitrogen double bond may exist as geometric isomers. Two methods are commonly used to designate the specific isomers, the "cis-trans" method and the "E and Z" method depending on whether the groups attached to each of the double bonded atoms are the same or different. A discussion of geometric isomerism and the naming of specific isomers is found in March, "Advanced Organic Chemistry", John Wiley & Sons, 1992, Chapter 4.

Compound (I) may be formulated as part of a pharmaceutical composition. As such, a pharmaceutical composition comprising Compound (I), or a pharmaceutically acceptable salt thereof, in combination with a pharmaceutically acceptable carrier, diluent or excipient is an important embodiment of the invention. Examples of pharmaceutical compositions and methods for their preparation are well known in the art. See, e.g. REMINGTON: THE SCIENCE AND PRACTICE OF PHARMACY (A. Gennaro, et al., eds., 19$^{th}$ ed., Mack Publishing (1995)). Illustrative compositions comprising Compound (I) include, for example:

Compound (I) in suspension with 0.5% carboxy methylcellulose, 0.25% Polysorbate 80 and 2.7% NaCl; or Compound (I) in suspension with 1% carboxy methylcellulose and 0.25% Polysorbate 80; Compound (I) in suspension with 1% carboxy methylcellulose, 0.25% Polysorbate 80, and 0.05% AntiFoam 1510™ in purified water; Compound (I) (jet milled) in suspension with 1% sodium carboxy methylcellulose, 0.25% Polysorbate 80, and 0.05% AntiFoam 1510™ in purified water; Compound (I) (jet milled) in suspension with 1% hydroxyethylcellulose, 10% Vitamin E TPGS (d-alpha-tocopheryl polyethylene glycol 1000 succinate), and 0.05% AntiFoam 1510™ in purified water; Compound (I) (jet milled) in suspension with 10% Vitamin E TPGS and 0.05% AntiFoam 1510™ in purified water; and Compound (I) in solution (15 mg/ml) with 20% Captisol®, 25 mM phosphate buffer (pH~2) and 1 eq. HCl. It will be understood, however, that a preferred composition of the present invention comprises Compound (I), or a pharmaceutically acceptable salt thereof, formulated in a capsule or tablet.

Compound (I), or a pharmaceutically acceptable salt thereof, or a composition comprising Compound (I) or a pharmaceutically acceptable salt thereof, can be administered by any route which makes the compound bioavailable, including oral and parenteral routes. It will be understood, however, that oral administration is preferred.

One of skill in the art will appreciate that particle size can affect the in vivo dissolution of a pharmaceutical agent which, in turn, can affect absorption of the agent. "Particle size" as used herein, refers to the diameter of a particle of a pharmaceutical agent as determined by conventional techniques such as laser light scattering, laser diffraction, Mie scattering, sedimentation field flow fractionation, photon correlation spectroscopy, and the like. Where pharmaceutical agents have poor solubility, small or reduced particle sizes may help dissolution and, thus, increase absorption of the agent. Amidon et al., *Pharm. Research*, 12; 413-420 (1995). Methods for reducing or controlling particle size (micronization) are conventional and include ball milling, pin milling, jet milling, wet grinding and the like. Another method for controlling particle size involves preparing the pharmaceutical agent in a nanosuspension. A particular embodiment of the present invention comprises Compound (I) or a pharmaceutically acceptable salt of Compound (I), or a pharmaceutical composition comprising Compound (I) or a pharmaceutically acceptable salt thereof, wherein said compound or salt has a d90 particle size (i.e. the size of which 90% of the particles are smaller than or equal to) of less than about 10 μm.

It will be appreciated by one skilled in the art that it is desirable for a therapeutic agent to possess certain physical characteristics. In particular, agents which are stable, crystalline solids are desired as they are particularly amenable to conventional paradigms of chemical synthesis, purification, storage, and formulation or dosage form development. "Crystalline form" or "crystal form" as used herein refers to a crystalline preparation of a chemical species.

A particular crystal form can be characterized and thus distinguished from other solid forms of the same chemical species using conventional techniques, including X-ray powder diffraction (XRPD), spectroscopic methods (e.g, infrared (IR) or nuclear magnetic resonance (NMR) spectroscopy), and thermal techniques (e.g differential scanning calorimetry (DSC), thermal gravimetric analysis (TGA), or differential thermal analysis (DTA)). While XRPD is a particularly useful means for characterizing crystal forms of a chemical species, it will be appreciated that the actual peak intensities in the X-ray pattern may vary from analysis to analysis of the same crystal form depending on the sample analyzed and the instrument, solvent, or procedures employed. In addition, it will also be understood that while the exact peak locations obtained from analysis of a given crystal form, as measured in °2θ, may vary from analysis to analysis (for example ±0.1°), the relative pattern of peak locations will remain essentially the same between spectra.

The present invention provides Compound (I) in crystalline form. More particularly, the present invention provides the free base of Compound (I) in crystalline form having characteristic peaks at °2θ of about 10.5, 13.0, 15.5, and 19.7 (free base Form I in the Examples herein). In addition, the present invention provides the free base of Compound (I) in crystalline form having characteristic peaks at °2θ of about 11.3, 12.1, 18.8, and 21.0 (free base Form II in the Examples herein).

As used herein the term "patient" refers to a human or nonhuman mammal such as a dog, cat, cow, monkey, horse, or sheep. More particularly, the term "patient" refers to a human. The term "treating" (or "treat" or "treatment") as used herein includes prohibiting, preventing, restraining, slowing, stopping, or reversing the progression or severity of an existing symptom or disorder. The term "preventing" (or "prevent" or "prevention") as used herein refers to prohibiting, restraining, or inhibiting the incidence or occurrence of a symptom or disorder. As appreciated by one of skill in the art, physiological disorders may present as a "chronic" condition, or as an "acute" episode. Thus, the treatment of disorders contemplates both acute events and chronic conditions. In an acute event, compound is administered at the onset of symptoms and discontinued when the symptoms disappear, whereas a chronic condition is treated throughout the course of the disease.

As used herein the term "effective amount" refers to the amount or dose of Compound (I), or a pharmaceutically acceptable salt thereof which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications.

When used in conjunction with the methods and uses of the present invention, the compound and compositions of the present invention may be administered either alone, or in combination with conventional therapeutic agents used to treat the particular disorder or condition. For example, Compound (I), or a composition comprising Compound (I) may be admistered in combination with conventional agents for the treatment of hypertension, diabetic nephropathy or chronic kidney disease such as angiotensin converting enzyme (ACE) inhibitors or angiotensin receptor blockers (ARB drugs). Where the compound or composition of the present invention is used as part of a combination, Compound (I), or a composition comprising Compound (I) may be administered either separately, or as part of a formulation comprising the therapeutic agent with which it is to be combined.

Determination of Biological Activity:

As used herein, "$K_d$" refers to the equilibrium dissociation constant for a ligand-receptor complex; "$K_i$" refers to the equilibrium dissociation constant for drug-receptor complex, and is an indication of concentration of drug that will bind to half the binding sites at equilibrium; "$K_b$" refers to the equilibrium dissociation constant for an antagonist-receptor complex; "IC50" refers to the concentration of an agent which produces 50% of the maximal inhibitory response possible for that agent or, alternatively, to the concentration of an agent which produces 50% displacement of ligand binding to the receptor; "EC50" refers to the concentration of an agent which produces 50% of the maximal response possible for that agent; and "ED50" refers to the dose of an administered therapeutic agent which produces 50% of the maximal response for that agent.

A. Steroid Nuclear Hormone Receptor Binding Assay:

Cell lysates from human embryonic kidney HEK293 cells overexpressing human MR (mineralocorticoid receptor), GR (glucocorticoid receptor), AR (androgen receptor), or PR (progesterone receptor) are used for receptor-ligand competition binding assays to determine $K_i$ values.

Briefly, steroid receptor competition binding assays are run in a buffer containing 20 mM HEPES buffer (pH=7.6), 0.2 mM EDTA, 75 mM NaCl, 1.5 mM $MgCl_2$, 20% glycerol, 20 mM sodium molybdate, 0.2 mM DTT (dithiothreitol), 20 μg/mL aprotinin and 20 μg/mL leupeptin (assay buffer). Typically, steroid receptor binding assays include radio-labeled ligands, such as 0.25 nM [$^3$H]-aldosterone for MR binding, 0.7 nM [$^3$H]-dexamethasone for GR binding, 0.36 nM [$^3$H]-methyltrienolone for AR binding, and 0.29 nM [$^3$H]-methyltrienolone for PR binding, and either 20 μg 293-MR lysate, 20 μg 293-GR lysate, 22 μg 293-AR lysate, or 40 μg 293-PR lysate per well. Assays are typically run in 96-well format. Competing test compounds are added at various concentrations ranging from about 0.01 nM to 10 μM. Non-specific binding is determined in the presence of 500 nM aldosterone for MR binding, 500 nM dexamethasone for GR binding, or 500 nM methyltrienolone for AR and PR binding. The binding reactions (140 μL) are incubated overnight at 4° C., then 70 μL of cold charcoal-dextran buffer (containing per 50 mL of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 μL of the binding reaction mixture is then transferred to another 96-well plate and 175 μL of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated IC50 and percentage inhibition at 10 μM. The $K_d$ for [$^3$H]-aldosterone for MR binding, [$^3$H]-dexamethasone for GR binding, [$^3$H]-methyltrienolone for AR binding, or [$^3$H]-methyltrienolone for PR binding, is determined by saturation binding. The IC50 values for compounds are converted to $K_i$ using the Cheng-Prusoff equation.

Following a protocol essentially as described above, Compound (I) displays a $K_i$ in the MR binding assay of about 0.40 nM, thus demonstrating that Compound (I) is a potent ligand of human MR. Furthermore, Compound (I) displayed a $K_i$ in the AR, GR, and PR binding assays of about 1170 nM, 669 nM, and 478 nM respectively, thus demonstrating that Compound (I) is a selective ligand for MR.

B. Functional Assays of Steroid Nuclear Hormone Receptor Modulation:

Aldosterone exerts it physiological effects through interaction with the mineralocorticoid receptor. Following cytoplasmic binding of aldosterone to MR, the ligand receptor complex translocates to the cell nucleus where it binds to hormone response elements on DNA to initiate expression of target genes. To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art.

1. Nuclear Hormone Receptor Panel Screen

Human embryonic kidney HEK293 cells are transfected with steroid hormone receptor and reporter gene plasmids using a suitable transfection reagent such as Fugene™. Briefly, the reporter plasmid containing two copies of probasin ARE and TK (thymidine kinase) promoter upstream of the luciferase reporter cDNA, is transfected into HEK293 cells with a plasmid constitutively expressing human androgen receptor (AR) using viral CMV (cytomegalovirus) promoter. The reporter plasmid containing two copies of GRE and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 µM. In the antagonist mode for the assays, low concentrations of agonist for each respective receptor are added to the media (0.08 nM aldosterone for MR, 0.25 nM dexamethasone for GR, 0.66 nM of methyltrienolone for AR, and 0.08 nM of promegestone for PR). After 24 hours incubation with test compounds, cells are lysed and luciferase activity is determined using standard techniques.

Data are fitted to a four parameter-fit logistic curve to determine EC50 values. The percentage efficacy (compounds with saturated maximum responses) or the percent maximum stimulation (compounds with maximum responses that do not saturate) are determined relative to maximum stimulation obtained with the following reference agonists: 30 nM aldosterone for MR assay, 100 nM methyltrienolone for AR assay, 30 nM promegestone for PR assay, and with 100 nM dexamethasone for GR assay. IC50 values are determined similarly using antagonist mode assay data. In the antagonist mode, percent inhibitions are determined by comparing test compound activity in the presence of low concentration of agonist (0.08 nM aldosterone for MR, 0.25 nM dexamethasone for GR, 0.66 nM of methyltrienolone for AR, and 0.08 nM of promegestone for PR) to the response produced by the same low concentration of agonist in the absence of test compound.

Following a protocol essentially as described above, Compound (I) displayed IC50 values of about 21 nM, 924 nM, >10000 nM, and >10000 nM in the MR, PR, GR, and AR assays (antagonist mode), respectively, and an EC50 of >10000 nM for each of MR, PR, GR, and AR in the agonist mode. Thus, Compound (I) is a selective functional antagonist of hMR.

2. hMR Competitive Antagonist Assay:

Human embryonic kidney HEK293 cells are transfected with human MR using the same transfection reagents, plasmids, promoters, reporter constructs, buffers, and procedures as described above for the Nuclear Hormone Receptor Panel Screen. Transfected cells are trypsinized, plated in 96 well dishes in DMEM media containing 5% charcoal-stripped FBS, incubated for 4 hours and then exposed to various concentrations (10 dilutions) of aldosterone (ranging from about 0.001 nM to 0.03 µM. The ability of aldosterone to agonize the hMR is determined in the absence and presence of fixed concentrations of test compound and is monitored by measuring luciferase activity using standard techniques. The test compound $K_b$ may then be determined using a Schild analysis plotting log (dose ratio—1) against log of antagonist concentration using the equation: Log (DR-1)=Log [Antagonist]−Log $K_b$ where the dose ratio (DR) represents the ratio of the aldosterone EC50 in the presence of test compound to the aldosterone EC50 in the absence of test compound).

Following a protocol essentially as described above, Compound (I) displayed a $K_b$ in the MR competitive antagonist assay of about 5.1 nM, thus demonstrating that Compound (I) is a potent antagonist of human MR.

C. In vivo Model of Aldosterone Mediated Renal Disease

Male uni-nephrectomized Sprague Dawley rats (240-280 g) are housed individually with ad lib house water and rodent 5001 diet for one week. After acclimation, baseline 24 h urine samples are collected and analyzed for total urine protein and creatinine. Animals are randomized via body weight and baseline urine protein into study groups. Baseline serum is taken by tail-clip and analyzed for blood urea nitrogen (BUN), creatinine, and electrolytes. After baseline samples are taken, all rats with the exception of the control group are maintained on a diet containing 6% salt, and drinking water containing 0.3% KCl throughout the study duration. Control animals are maintained on 5001 diet and house water throughout the study duration and do not receive aldosterone. Alza mini-pumps to deliver 2.5 µl/h×28 days of d-aldosterone in 0.01% DMSO at 0.75 µg/h, s.c. are implanted in non-control animals (e.g Test Compound group and Vehicle only group) under isoflourane anesthesia. Test compound, in a vehicle comprising 1% carboxy methylcellulose (CMC)/0.25% polysorbate 80, or vehicle alone, is then administered by once daily oral gavage (10 mL/kg) beginning the day after aldosterone implantation. Repeat urine samples are collected after 2 and 4 weeks of compound or vehicle alone administration and analyzed for total urine protein and creatinine. At study termination, pharmacokinetic samples are obtained at 8 timepoints (0.5, 1, 2, 3, 6, 8, 12 and 24 h). In addition, hearts and kidneys may be removed and fixed in 10% buffered formalin for haematoxylin and eosin (H&E) and Masson's trichrome staining to detect structural damage in cardiac and renal tissues. Serum may also be taken by cardiac puncture at study termination for additional analysis of serum BUN, creatinine, and electrolytes.

Following a protocol essentially as described above, Compound (I), when administered at 10 mg/kg/day×28 days, reduced urinary protein excretion compared to vehicle treated animals by about 60%, thus demonstrating that Compound (I) has potent in vivo reno-protective activity.

In order to demonstrate that a compound has antihypertensive effects, the following model may be employed.

D. In Vivo Model of Aldosterone Mediated Hypertension

Male uni-nephrectomized Sprague Dawley rats (240-280 g) are housed individually with ad lib house water and rodent 5001 diet for one week. After acclimation, animals are implanted with Alzet pumps to subcutaneously deliver 0.25 µg/h of aldosterone at 2.5 µl/h for up to 28 days, and maintained on a diet containing 6% NaCl and drinking water containing 0.3% KCl throughout the duration of the study. Radiotelemetry devices are also implanted to monitor arterial blood pressure. For example, signals from each animal are sampled every 10 minutes throughout the study. The mean (±SEM) of all values collected over a twenty four hour period represent the mean daily arterial pressure for each animal.

On the day following pump implantation, test compound in a vehicle comprising 1% medium viscosity sodium carboxy methylcellulose/0.25% polysorbate 80/0.05% Antifoam 1510 ™, or vehicle alone, is then administered by once daily oral gavage (10 mL/kg).

Following a protocol essentially as described above, Compound (I), when orally administered once daily (1-30 mg/kg/day)×14 days, dose dependently reduced the hypertensive effects of aldosterone in the presence of salt compared to vehicle, thus demonstrating that Compound (I) has antihypertensive effects.

In order to demonstrate that a compound has a reduced incidence or likelihood of producing hyperkalemia, the following model may be employed.

E. In Vivo Assay of Electrolyte Modulation

Male Sprague Dawley rats (240-280 g) are adrenalectomized then maintained on 5001 rodent chow and 1% NaCl drinking solution for 6 days after surgery. Animals are then fasted overnight and 1% saline drinking water is replaced with house water ad lib. The morning of the study, fasted animals are randomized to treatment on the basis of fasted body weight. Control animals (e.g. those that receive no aldosterone or test compound) are given 10 mL/kg of test compound vehicle comprising 0.5% CMC/0.25% polysorbate 80/2.7% NaCl by oral gavage, and 1 mL/kg of aldosterone vehicle (0.01% DMSO/water) by subcutaneous injection. Vehicle animals are given the same test compound vehicle by oral gavage and aldosterone 3 µg/kg, s.c. Test substances are suspended in the carboxy methylcellulose/NaCl vehicle. The test compound treatment groups receive test substance suspended in the carboxy methylcellulose/NaCl vehicle and aldosterone 3 µg/kg s.c. Immediately after dosing, animals are placed in metabolic racks with ad lib access to house water. Urine samples are collected 5 hours after dose administration and electrolyte excretion is assayed. Data are presented as log Na/K excretion ratio or % of Na/K ratio with respect to adrenalectomized vehicle treated animals. Compound I can be tested at various doses to determine to what extent the compound induces an increase in the urinary Na/K ratio (an index of increased serum potassium concentration).

Following a protocol essentially as described above, Compound (I), when administered at 30 mg/kg p.o., increased the urinary Na/K excretion ratio by only about 30% compared to vehicle treated animals demonstrating that Compound (I) may have a reduced incidence or likelihood of producing hyperkalemia.

Without further elaboration, it is believed that one skilled in the art can use the preceding description to practice the present invention to its fullest extent. The following Preparations and Example are provided to illustrate the invention in further detail and represent typical synthesis of Compound (I). The reagents and starting materials are readily available to, or may be readily synthesized by, one of ordinary skill in the art. Those skilled in the art will promptly recognize appropriate variations from the procedures described in the examples. The names of the compounds of the present invention are generally as provided by ChemDraw Ultra® version 10.0.

As used herein, the following terms have the meanings indicated: "DMSO" refers to dimethyl sulfoxide; "DMAC" refers to N,N-dimethylacetamide; "tBOC" or "boc" refers to tert-butoxycarbonyl; and "TLC" refers to thin layer chromatography.

PREPARATION 1

1-Bromo-4-fluoro-2-(2-iodo-benzyloxy)-benzene

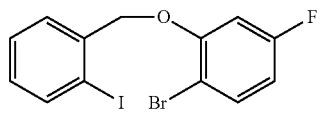 [SMILES: Fc1ccc(Br)c(OCc2ccccc2I)c1]

Stir a mixture of 2-iodobenzyl bromide (90 g, 0.29 mol), 2-bromo-5-fluorophenol (57.9 g, 0.29 mol), and potassium carbonate (63 g, 0.46 mol) in N,N-dimethylformamide (750 mL) at room temperature for 16 h. Add water (1 L), stir the resulting mixture for one hour, filter off solids, rinse with water and dry in a vacuum oven (20 mm Hg/60° C.) to obtain the title compound (121 g, >100%). $^1$H NMR (400 MHz, DMSO-$d_6$) δ 5.11 (s, 2H), 6.81 (t, 1H), 7.13 (t, 1H), 7.19 (dd, 1H), 7.46 (t, 1H), 7.59 (d, 1H), 7.62 (t, 1H), 7.93 (d, 1H).

PREPARATION 2

3-[2-(2-Bromo-5-fluoro-phenoxymethyl)-phenyl]-acrylic Acid Ethyl Ester

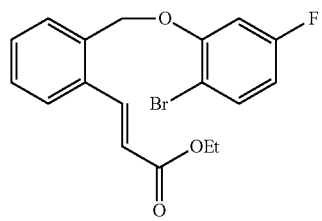 [SMILES: CCOC(=O)/C=C/c1ccccc1COc1cc(F)ccc1Br]

To a mixture of 1-bromo-4-fluoro-2-(2-iodo-benzyloxy)-benzene (117.4 g, 0.29 mol), sodium acetate (36.1 g, 0.44 mol), tetra-n-butylammonium bromide (90.3 g, 0.29 mol), palladium (II) acetate (1.8 g, 8 mmol, 3 mol %), and N-methylpyrrolidinone (900 mL) at 55-60° C., add dropwise a solution of ethyl acrylate (34.3 mL, 0.32 mol) in N-methylpyrrolidinone (200 mL). Cool the reaction mixture to room temperature and treat with water (2 L) and methyl tert-butyl ether (2 L). Pass the reaction through diatomaceous earth, add ethyl acetate (1 L), separate the layers, and wash with water (2 L). Dry the organic portion over anhydrous sodium sulfate, filter, and concentrate. Suspend the resulting solid in hexanes (1 L), refrigerate for 2 h, filter, and wash with cold hexanes (500 mL). Dry in a vacuum oven (50° C./20 mm Hg) to obtain the title compound as a pale yellow solid (104.4 g, 95%). LC-MS m/z 381.0 [M+H]$^+$.

Alternate Procedure:

To a clean, dry 100-gallon reactor with stirring under nitrogen add fresh N-methylpyrrolidinone (72 L), sodium acetate (2721 g, 33.17 mol), 1-bromo-4-fluoro-2-(2-iodo-benzyloxy)-benzene (9000 g, 22.11 mol) and tetrabutylammonium bromide (7128 g, 22.11 mol). Initiate stirring and de-gas the reaction mixture under full vacuum for 30 min, purging with nitrogen. Allow the reactor to return to ambient pressure under nitrogen and repeat the degassing procedure. Add palladium (II) acetate (180 g, 2%/weight) to the reaction mixture and heat to 60° C. At 60° C., slowly add ethyl acrylate (2258 g, 22.55 mol) as a solution in N-methyl pyrrolidinone (18 L) to the reaction mixture via the addition funnel. Upon completion of the addition, heat the reaction mixture to 70° C. Continue to stir for a minimum of 2 h at 70° C. Adjust the internal temperature of the reaction mixture to 5-10° C. To a separate, clean, appropriately sized reactor, charge water (225 L), initiate vigorous stirring and cool to an internal temperature of ≤5° C. Transfer the reaction mixture to the vigorously stirring water over a minimum of one hour. Stir the resulting suspension for 30 min to one hour at ambient temperature. Filter through a polypropylene filter pad to collect the light purple solids. Wash the filter cake with water (25 L) and pull dry on the filter using a rubber dam. Recharge the solids to the reactor with water (45 L) and stir the suspension for 30 min to one hour. Re-filter the solids onto a polypropylene filter pad, washing the filter cake with water (25 L). Pull dry on the filter using a rubber dam. Transfer the light purple material to drying trays and air dry in a fume hood for a minimum of 24 h. Oven dry the solids under vacuum at <50° C. to obtain the title compound (8.4 kg, 100%).

PREPARATION 3

(E)-(3-Fluoro-6H-dibenzo[b,e]oxepin-11-ylidene)-acetic Acid Ethyl Ester

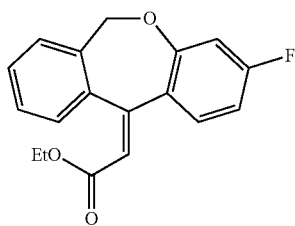 [SMILES: CCOC(=O)/C=C1\c2ccccc2COc2cc(F)ccc21]

Heat a mixture of 3-[2-(2-bromo-5-fluoro-phenoxymethyl)-phenyl]-acrylic acid ethyl ester (94 g, 0.25 mol), sodium acetate (30 g, 0.37 mol), tetra-n-butylammonium bromide (81 g, 0.25 mol), and palladium (II) acetate (1.7 g, 7 mmol, 3 mol %) in N-methylpyrrolidinone (850 mL) at 100-110° C. for 6 h. Cool to room temperature, dilute with water (1 L), filter through diatomaceous earth, and wash with ethyl acetate (2 L). Transfer the filtrate to a separatory funnel, add water (500 mL) and separate the layers. Wash the organic layer with water (2×1.5 L), dry over anhydrous sodium sulfate, filter through a silica pad, wash with ethyl acetate (1.5 L) and concentrate to dryness. To the residual solid add hexanes (1 L), refrigerate for 2 h, filter, rinse with hexanes (500 mL), and dry at 50° C./20 mm Hg to obtain the title compound (64.3 g, 87%). LC-MS m/z 299.0 [M+H]$^+$.

Alternate Procedure:

To a clean, dry 100-gallon reactor with stirring under nitrogen add N-methyl pyrrolidinone (83.4 L), sodium acetate (2.706 kg, 32.98 mol), 3-[2-(2-bromo-5-fluoro-phenoxymethyl)-phenyl]-acrylic acid ethyl ester (9.256 kg, 21.99 mol) and tetrabutylammonium bromide (7.088 kg, 21.99). Initiate stirring and de-gas the reaction mixture under full vacuum for 30 min, purging with nitrogen. Allow the reactor to return to ambient pressure under nitrogen and repeat the degassing procedure. Add palladium (II) acetate (167 g, 2% weight) to the reaction mixture. Heat the reaction to between 100° C. and 125° C., stirring for a minimum of 3 to 5 h. Add ethyl acetate (100 L) and stir 30 min. Add water (100 L) and stir 30 min. Discontinue stirring and allow the layers to separate for a minimum of one hour. Collect the organic layer and extract the aqueous layer with ethyl acetate (50 L, then 25 L). Combine the organic portions and wash with water (40 L), a 20% aqueous sodium chloride solution (2×20 L), stirring for a minimum of 30 min each and allowing at least 30 min for layer separation. Dry the organic solution with magnesium sulfate (8.0 kg) and add activated carbon (2.0 kg) and silica gel 60 (2.0 kg), stirring for a minimum of one hour. Filter to remove the solids. Concentrate the filtrate to dryness under vacuum at <35° C. Add methanol (20 L) to the solid residue and heat the mixture to a clear solution at 50-60° C. Add heptane (40 L) and cool to between 20° C. and 25° C. Continue to further cool the reaction mixture to −10° C. over a minimum of 3 h. Stir at −10° C. for a minimum of 12 h. Filter to collect the resulting solid product, washing with a mixture of heptane:methanol, (75:25) (2×20 L). Dry the solids under vacuum at <40° C. to a constant weight to obtain the title compound (3.7 kg, 64%).

Alternate Procedure 2:

Heat 1-bromo-4-fluoro-2-(2-iodo-benzyloxy)-benzene (50 g, 0.123 mol), sodium acetate (30.2 g, 0.369 mol), tetrabutylammonium bromide (39.6 g, 0.123 mol), and palladium acetate (1 g) in N-methylpyrrolidine (250 mL) to 60° C. Add ethyl acrylate (12.91 g, 0.129 mol) in N-methylpyrrolidine (50 mL) dropwise over 20 min. After the addition is complete, heat the reaction mixture to 145° C. for 3 h. Cool the reaction mixture to room temperature, filter through diatomaceous earth, and wash the solids with methyl t-butyl ether (2×150 mL). Dilute the filtrate with methyl t-butyl ether (0.5 L) and wash with water (0.5 L). Separate the organic layer and extract the aqueous layer with methyl t-butyl ether (2×300 mL). Wash the combined organic layers with water (2×200 mL). Dry the organic portion over magnesium sulfate, treat with charcoal, filter, wash the solids with methyl t-butyl ether (100 mL) and concentrate. Slurry the residue in isopropanol (20 mL) in a Buchi flask at 55° C. without vacuum. Add heptanes (100 mL) with stirring. Place the dark suspension in a cold room overnight. Filter the solids, rinse with cold heptane/isopropanol (9:1, 2×100 mL), then heptane (50 mL) and dry to a constant weight in a vacuum oven at 35° C. to obtain the title compound as a tan powder (22.25 g, 61%).

PREPARATION 4

(E)-11-Bromomethylene-3-fluoro-6,11-dihydro-dibenzo[b,e]oxepine

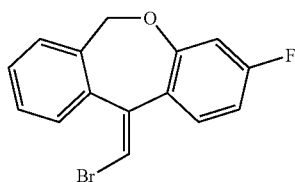 [SMILES: Fc1ccc2c(c1)OCc1ccccc1/C2=C\Br]

To a suspension of (3-fluoro-6H-dibenzo[b,e]oxepin-11-ylidene)-acetic acid ethyl ester (69.5 g, 0.23 mol) in isopropanol (725 mL) add a solution of lithium hydroxide (12.0 g, 0.53 mol) in water (125 mL) and warm to 70° C. for 4 h. Allow the mixture to cool to 40° C. and then treat with glacial acetic acid (0.44 mol, 25 mL). After stirring for 15 min, add N-bromosuccinimide (0.25 mol, 44 g). Bubbling ensues, the temperature rises to 45° C., and solids form after a few minutes. Stir the mixture at 40-45° C. for one hour and cool to room temperature. Add sodium bisulfite (4.5 g) in water (150 mL), saturated aqueous sodium bicarbonate (150 mL), and water (450 mL). Filter the resulting suspension and rinse with cold 1:1 isopropanol/water (300 mL). Dry the solid at 60° C./20 mm Hg overnight to obtain the title compound (65.8 g, 93%). $^1$H NMR (400 MHz, DMSO-d$_6$) δ 4.9-5.4 (br d, 2H), 6.63 (dd, 1H), 6.77 (dt, 1H), 7.13 (s, 1H), 7.32-7.46 (m, 4H), 7.52 (dd, 1H).

Alternate Procedure:

To a clean, dry 100-gallon reactor with stirring under nitrogen, charge isopropanol (125 L), (E)-(3-fluoro-6H-dibenzo[b,e]oxepin-11-ylidene)-acetic acid ethyl ester (13.857 kg, 46.42 mol), and a solution of lithium hydroxide (3.896 kg, 92.84 mol) in water (54 L). Heat the reaction mixture to 80° C. and stir for 2 h. Cool the reaction mixture to 40° C. and add acetic acid (5.575 kg, 92.84 mol) over 20 min between 40° C. and 45° C. Add N-bromosuccinimide (48.74 mol, 8.676 kg) portion-wise over 30 min at <45° C. Cool the reaction to room temperature and stir for a minimum of 12 h. Add an aqueous solution of sodium bisulfite (~37.7 L) and stir 15 min. Add an aqueous solution of sodium bicarbonate (~37.7 L) and stir 15 min. Add water (129 L) and stir 30 min. Filter to collect the resulting solids, washing with isopropanol:water (1:1, 2×20 L). Dry the solids under vacuum at 32° C. to a constant weight to obtain the title compound (13.8 kg, 97%).

PREPARATION 5

(E)-2-((3-fluorodibenzo[b,e]oxepin-11 (6H)-ylidene) methyl)-4,4,5,5-tetramethyl-1,3,2-dioxaborolane

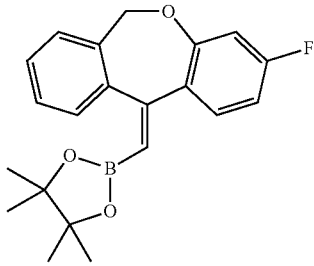 [SMILES: CC1(C)OB(/C=C2\c3ccccc3COc3cc(F)ccc32)OC1(C)C]

To a stirred mixture of (E)-11-(bromomethylene)-3-fluoro-6,11-dihydrodibenzo[b,e]oxepine (15 g, 49 mmol) and bis(pinacolato)diboron (16 g, 64 mmol) in 1,4-dioxane (250 mL) add potassium acetate (15 g, 150 mmol). Flush the mixture with nitrogen, add dichloro[1,1'-bis(diphenylphosphino)-ferrocene] palladium(II) dichloromethane adduct (1.80 g, 2.46 mmol), and heat at 65° C. overnight. Cool to room temperature, filter through diatomaceous earth, wash with ethyl acetate, and concentrate the filtrate in vacuo. Add methanol (200 mL) and rotate the mixture for one hour on a rotory evaporator without vacuum, causing a brown solid to form. Collect the dark brown crystals by filtration and dry under vacuum overnight to obtain the title compound (7.28 g, 42%). Concentrate the filtrate and purify by column chromatography eluting with 0% to 16% ethyl acetate in hexanes to obtain the title compound as a yellow solid (3.46 g, 20%). Total yield for the reaction is 10.7 g (62%). $^1$H NMR (300 MHz, CDCl$_3$) δ 7.36 (dd, J=8.8, 6.8 Hz, 1H), 7.32-7.27 (m, 4H), 6.64-6.57 (m, 1H), 6.48 (dd, J=10.3, 2.6 Hz, 1H), 5.98 (s, 1H), 5.20 (br s, 1H), 1.15 (s, 12H).

Alternate Procedure:

Equip a 50 L three-neck round-bottom flask with a mechanical stirrer, thermocouple, nitrogen inlet, and reflux condenser. Place into a heating mantle. Charge the flask with dioxane (13.5 L), (E)-11-bromomethylene-3-fluoro-6,11-dihydro-dibenzo[b,e]oxepine (1.600 kg, 5.24 mol), bis(pinacolato)diboron (1.731 kg, 6.82 mol), potassium acetate (823 g, 8.38 mol), water (20 mL), tricyclohexyl phosphine (29.5 g, 0.105 mol), and tris(dibenzylidene acetone)di-palladium (48 g, 0.052 mol). Heat the reaction mixture to 80-85° C. Maintain the reaction at 85-90° C. for a minimum of 6 h. Cool to room temperature. Filter the reaction mixture through a pad of diatomaceous earth (2-3 in). Wash the filtrate with ethyl acetate (2×3.5 L). Concentrate the filtrate on a rotory evaporator at 50-55° C. Co-evaporate with heptanes (2×3.5 L) to form a suspension. Add methanol (2.5 L) to the slurry at 50° C. Stir for 10-15 min. Cool the slurry to −10-0° C. for 20-30 min. Filter the solid. Wash the collected solids with cold (−10° C.) methanol (2×1.5 L), followed by heptanes (2×1.5 L). Dry the solids under vacuum at ambient temperature to afford the title compound as an off-white solid (1.408 kg, 76%).

PREPARATION 6

(2R,4R)-4-Hydroxy-pyrrolidine-2-carboxylic acid hydrochloride

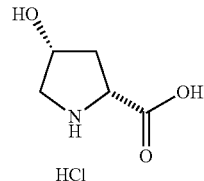

Following a procedure essentially as described in Tetrahedron: Asymmetry, 14, (2003) 3141-3152, to a mixture of acetic anhydride (1.437 kg, 5.65 eq) and acetic acid (4.225 L) at 50° C. add trans-4-hydroxy-L-proline (331 g, 2.49 mol) in portions over 30 min. Heat the reaction mixture for 5.5 h at 90° C. then allow to cool to room temperature. Stir the reaction at room temperature overnight and then concentrate. Dissolve the residue in 2 N hydrochloric acid (4.57 L) and reflux for 3 h. Cool the reaction mixture to room temperature, filter through diatomaceous earth, and concentrate under vacuum at 70° C. to approximately 700 mL. Allow the material to cool to room temperature and let sit overnight. Dilute the resulting slurry with ether (1 L), filter the crystals, wash with ether, and dry under vacuum to obtain the title compound (340 g). Dissolve the solid in hot ethanol (2.5 L), cool, stir slowly at 35° C., and add ether (2.5 L) slowly in portions over one hour. Stir for 2 h, filter the resulting white solid, and dry overnight in a vacuum oven to obtain the title compound (270.6 g, 65%). [α]$_D^{20}$+12.0 (c=1.0 in methanol). $^1$H NMR (400 MHz, D$_2$O), δ 2.34-2.39 (m, 1H), 2.45-2.53 (m, 1H), 3.38 (dd, 1H), 3.45 (d, 1H), 4.50 (dd, 1H), 4.58 (br s, 1H).

PREPARATION 7

(2R,4R)-4-Hydroxy-pyrrolidine-1,2-dicarboxylic acid 1-tert-butyl ester 2-methyl ester

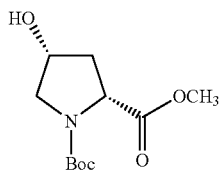 [SMILES: COC(=O)[C@H]1C[C@@H](O)CN1C(=O)OC(C)(C)C]

Add thionyl chloride (233 mL, 3.10 mol) drop wise to a solution of (2R, 4R)-4-hydroxy-pyrrolidine-2-carboxylic acid hydrochloride (355 g, 2.12 mol) in dry methanol (3.5 L) at 0° C. under a nitrogen atmosphere. Upon complete addition, warm the reaction mixture to room temperature and stir for 6 h. Concentrate the reaction mixture under reduced pressure to obtain the corresponding methyl ester hydrochloride as a waxy solid. Suspend the solid in dry dichloromethane (3.5 L) at 0° C. and add triethylamine (640 mL, 4.66 mol) cautiously over 30 min and stir for an additional 30 min. Add N,N-dimethylaminopyridine (39 g, 0.32 mol) and di-tert-butyl dicarbonate (500 g, 2.25 mol) consecutively. Warm the reaction mixture to room temperature and stir for 18 h. Extract the solution with water (4 L), saturated sodium bicarbonate (4 L), and brine (4 L). Treat the organic layer with ethylenediamine (8 mL), stir for 15 min, and back-extract with 10% aqueous citric acid (4 L). Dry the organic layer over anhydrous sodium sulfate, filter, and concentrate under vacuum to obtain a yellow oil (484 g), which solidifies overnight. Dissolve in methyl t-butyl ether (1 L) and concentrate to low volume. Add hexanes (2 L) and allow the mixture to stand for one hour. Filter the white solids and wash with hexanes. Dry the white solid (20 mm Hg/60° C.) overnight to obtain the title compound (354 g, 68%). $[\alpha]D^{20}$+56.3 (c=1.0 in methanol). $^1$H NMR (400 MHz, CDCl$_3$) δ 1.43 (s, 9H), 1.46 (s, 9H), 2.05-2.10 (m, 2H), 2.26-2.35 (m, 2H), 3.48-3.56 (m, 2H), 3.58-3.61 (m, 1H), 3.64-3.70 (m, 2H), 3.77 (s, 3H), 3.79 (s, 3H), 4.27-4.29 (m, 1H), 4.34-4.38 (m, 2H).

PREPARATION 8

(2R,4S)-4-Bromo-pyrrolidine-1,2-dicarboxylic acid 1-tert-butyl ester 2-methyl ester

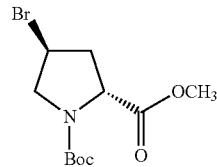

To a solution of (2R,4R)-4-hydroxy-pyrrolidine-1,2-dicarboxylic acid 1-tert-butyl ester 2-methyl ester (320 g, 1.30 mol) and carbon tetrabromide (540 g, 1.94 mol) in dichloromethane (3.2 L) at 0-5° C. (dry ice/dichloromethane bath) add triphenylphosphine (1.95 mol, 514 g) in portions over 30 min and stir at room temperature for 4 h. Add ethanol (3.2 L) and stir for an additional 2 h. Transfer the reaction to an 18 L carboy and add ether (8 L) until precipitation occurs. Stir the mixture overnight. Filter off the solids and concentrate the ether layer. Dissolve the oily residue in dichloromethane and filter through a silica plug eluting with dichloromethane until no more product can be detected by TLC. Concentrate the dichloromethane layer and treat with 5% ethyl acetate in hexanes (4 L) causing a white solid to form. Pass the mixture through a silica plug eluting with 5% ethyl acetate in hexanes and collect only the fractions that contain the desired product. Concentrate the solution, dissolve in 5% ethyl acetate in hexanes (2 L) and purify through a 1 kg silica gel pad eluting with 5% ethyl acetate in hexanes to obtain the title compound as a yellowish oil (372.4 g, 93%). $[\alpha]D^{20}$+53.6 (c=1.0 in methanol). $^1$H NMR (400 MHz, DMSO-d$_6$) δ 1.33 and 1.39 (two s, 9H), 2.40 (m, 1H), 2.53 (m, 1H), 3.35 (m, 1H), 3.66 (s, 3H), 3.80 (m, 1H), 4.35 (q, 1H), 4.73 (m, 1H).

PREPARATION 9

(2R,4R)-4-Azido-pyrrolidine-1,2-dicarboxylic acid 1-tert-butyl ester 2-methyl ester

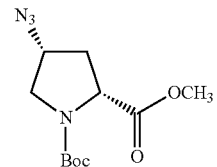 [SMILES: COC(=O)[C@H]1C[C@@H](N=[N+]=[N-])CN1C(=O)OC(C)(C)C]

Add sodium azide (157 g, 2.39 mol) to (2R,4S)-4-bromo-pyrrolidine-1,2-dicarboxylic acid 1-tert-butyl ester 2-methyl ester (370 g, 1.20 mol) in N,N-dimethylformamide (2.5 L) and heat at 70-75° C. for 16 h under nitrogen. Cool to room temperature, dilute with water (5 L), and extract with ethyl acetate (3 L). Wash with brine (2 L). Extract the brine layer with ethyl acetate (3 L), combine the organic layers, dry over sodium sulfate, filter and concentrate to obtain an oil (324.5 g). Dissolve the material in ether (2 L), wash with water (2×2 L), dry over sodium sulfate, filter, and concentrate to obtain 261.2 g of a dark yellow oil. Back-extract the aqueous layer with ether (2×2 L), dry over sodium sulfate, filter, and concentrate to obtain an additional 7.3 g of product. Overall yield 268.5 g (83%). $[\alpha]D^{20}$+39.5 (c=1.0 in methanol). $^1$H NMR (400 MHz, CDCl$_3$) δ 1.40-1.41 (s, 9H), 2.09-2.13 (m, 1H), 2.40-2.44 (m, 1H), 3.37-3.45 (m, 1H), 3.61-3.65 (m, 1H), 3.67-3.69 (s, 3H), 4.09-4.15 (m, 1H), 4.25-4.38 (m, 1H).

PREPARATION 10

(2R,4R)-4-Azido-2-hydroxymethyl-pyrrolidine-1-carboxylic acid tert-butyl ester

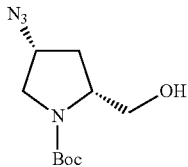

Add lithium borohydride (8.50 g, 351 mmol) to a solution of (2R,4R)-4-azido-pyrrolidine-1,2-dicarboxylic acid 1-tert-butyl ester 2-methyl ester (95 g, 351 mmol) in ether (1 L) at −30° C. under nitrogen. Allow the temperature to rise to 0° C. over 1.5 h and stir for an additional 2 h. Cool to −70° C. and add saturated aqueous sodium bicarbonate (1 L) dropwise. Allow to warm to room temperature, separate the layers and extract the aqueous layer with ether (1 L). Combine the ether layers, dry over sodium sulfate, filter, and concentrate. Dry the resulting material under high vacuum to obtain a yellow oil (82 g, 96%). $[\alpha]D^{20}$+20.3 (c=1.0 in methanol). $^1$H NMR (400 MHz, DMSO-d$_6$) δ 1.38 (s, 9H), 1.99 (br s, 1H, OH), 2.20 (m, 1H), 3.34 (m, 1H), 3.50-3.78 (m, 1H), 4.29 (m, 1H), 4.78 (m, 1H).

PREPARATION 11

(2R,4R)-4-Amino-2-hydroxymethyl-pyrrolidine-1-carboxylic acid tert-butyl ester

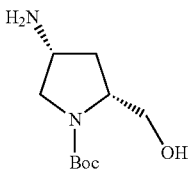

Hydrogenate a mixture of (2R,4R)-4-azido-2-hydroxymethyl-pyrrolidine-1-carboxylic acid tert-butyl ester (225 g, 0.93 mol) and 10% palladium on carbon (22.5 g, pre-wetted with toluene) in methanol (2.3 L) at 15 psi of hydrogen at room temperature for 16 h. Filter off the catalyst and concentrate the filtrate to obtain the title compound as an oil (198 g, 92%). $^1$H NMR (400 MHz, DMSO-$d_6$) δ 1.38 (s, 9H), 1.58 (m, 1H), 2.16 (m, 1H), 2.95 (m, 1H), 3.20-3.58 (m, 6H), 3.61 (m, 1H), 3.65 (br s, 1H).

PREPARATION 12

(2R,4R)-4-(4-Bromo-2-nitro-phenylamino)-2-hydroxymethyl-pyrrolidine-1-carboxylic acid tert-butyl ester

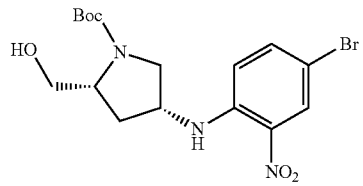

Reflux a mixture of (2R,4R)-4-amino-2-hydroxymethyl-pyrrolidine-1-carboxylic acid tert-butyl ester (198 g, 0.92 mol), 5-bromo-fluoronitrobenzene (224 g, 0.98 mol), triethylamine (273 mL, 1.96 mol) in ethyl acetate (2 L) for 16 h under nitrogen with vigorous stirring. Cool to room temperature and wash with brine. Back-extract the brine layer with ethyl acetate (1 L), combine the organic layers, dry over sodium sulfate, filter and concentrate. Dissolve the resulting solid in warm ethyl acetate (2 L), concentrate to approximately 500 mL and allow crystals to start forming Treat the solution slowly with hexanes (2 L) and allow the mixture to stand at room temperature for 2 h. Collect the yellow solid by filtration, wash with hexanes and dry at 40° C./20 mm Hg to obtain 227 g of desired product. The filtrate is concentrated under reduced pressure and the residue is purified by silica gel column chromatography (2:3:5 ethyl acetate/dichloromethane/heptane gradually increasing to 2:3 ethyl acetate/heptane) to obtain an additional 54 g of desired product. Overall yield: 281 g (70%). [α]$D^{20}$ –81 (c=1.0 in methanol). $^1$H NMR (400 MHz, DMSO-$d_6$) δ 1.40 (s, 9H), 1.90 (m, 1H), 2.48 (br s, 1H), 3.14 (m, 1H), 3.45 (m, 1H), 3.63 (m, 1H), 3.81 (m, 2H), 4.29 (m, 1H), 5.12 (m, 1H), 7.08 (d, 1H), 7.65 (dd, 1H), 8.15 (d, 1H), 8.57 (br d, 1H, NH).

PREPARATION 13

(2R,4R)-[4-(4-Bromo-2-nitro-phenylamino)-pyrrolidin-2-yl]-methanol, hydrochloride

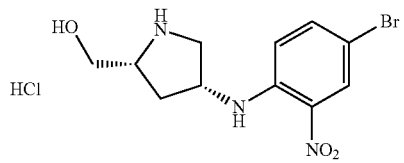 [SMILES: Cl ; O=[N+]([O-])c1cc(Br)ccc1N[C@H]1CN[C@@H](CO)C1]

To a solution of (2R,4R)-4-(4-bromo-2-nitro-phenylamino)-2-hydroxymethyl-pyrrolidine-1-carboxylic acid tert-butyl ester (125.5 g, 0.301 mol) in dichloromethane (400 mL) add 4 N hydrochloric acid in dioxane (800 mL) and stir for 4 h at room temperature. Collect the precipitate by filtration, wash with ether and dry at 20 mm Hg/60° C. to obtain the title compound (105.2 g, 99%). [α]$D^{20}$ –89.6 (c=1.0 in methanol). $^1$H NMR (400 MHz, DMSO-$d_6$) δ 1.80-1.85 (m, 1H), 2.54-2.59 (m, 1H), 3.43-3.51 (m, 3H), 3.56-3.63 (m, 1H), 3.69-3.72 (m, 2H), 4.50-4.51 (m, 1H), 5.60 (br s, 1H), 7.10 (d, 1H), 7.65 (dd, 1H), 8.14 (d, 1H), 8.95 (br s, 1H), 9.91 (br s, 1H).

PREPARATION 14

(7R,8aR)-7-(4-Bromo-2-nitro-phenylamino)-tetrahydro-pyrrolo[2,1-c][1,4]oxazin-4-one

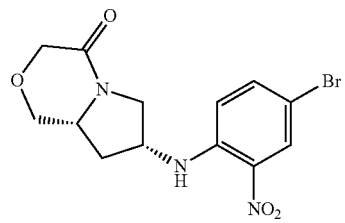 [SMILES: O=C1COC[C@H]2C[C@@H](Nc3ccc(Br)cc3[N+](=O)[O-])CN12]

To a stirring solution of (2R,4R)-[4-(4-(4-bromo-2-nitro-phenylamino)-pyrrolidin-2-yl]-methanol, hydrochloride (54.5 g, 155 mmol) in tetrahydrofuran (375 mL) and water (376 mL) add 5 N sodium hydroxide dropwise until the pH is 10-12. Add chloroacetyl chloride (27.3 mL, 337 mmol) through a dropping funnel dropwise over 30 min. Using another dropping funnel, add 5 N sodium hydroxide during the addition of the acid chloride at such a rate as to maintain the internal pH at 8-12. Stir for 6 h, collect the solid that has formed by filtration and wash with water. Remove the organic component of the filtrate under reduced pressure and collect the solids by filtration. Combine the two solid batches and dry at 60° C./20 mm Hg to obtain 51.4 g. Suspend the solid in 2% methanol in dichloromethane (1.5 L) and rotate on a rotary evaporator at 40° C. for one hour. Collect the precipitate by filtration (11 g) and discard. Pass the filtrate through a silica gel plug eluting with dichloromethane and concentrate the eluent to obtain the title compound as a yellow orange solid (32.8 g, 60%). $^1$H NMR (400 MHz, DMSO-$d_6$) δ 1.68 (m, 1H), 2.42 (m, 1H), 3.37 (m, 1H), 3.49 (m, 1H), 3.75-3.91 (m, 3H), 4.10 (m, 2H), 4.48 (m, 1H), 7.18 (d, 1H), 7.64 (dd, 1H), 7.93 (d, 1H), 8.19 (s, 1H).

PREPARATION 15

(7R,8aR)-(4-Bromo-2-nitro-phenyl)-(hexahydro-pyrrolo[2,1-c][1,4]oxazin-7-yl)-amine

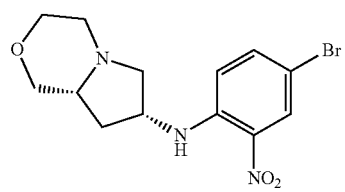 [SMILES: O=[N+]([O-])c1cc(Br)ccc1N[C@@H]1C[C@@H]2COCCN2C1]

Add (7R,8aR)-7-(4-bromo-2-nitro-phenylamino)-tetrahydro-pyrrolo[2,1-c][1,4]oxazin-4-one (32.1 g, 90.1 mmol) to anhydrous tetrahydrofuran (450 mL) and cool at 0 to –5° C. Add borane-dimethylsulfide complex (26 mL, 0.279 mol) over 10 min. Heat the mixture to reflux for 3 h. Cool the reaction mixture in an ice bath and cautiously add methanol (450 mL) dropwise. Add 4 N hydrochloric acid (450 mL) and reflux for 2 h. Cool to approximately 40° C. and adjust the pH to 10-12 with cautious dropwise addition of 5 N sodium hydroxide. Remove the organic solvent under reduced pressure. Dilute the aqueous layer with water (1.2 L) and extract with dichloromethane (1.2 L). Dry the organic layer over sodium sulfate, filter, and concentrate to obtain an oil. At this point combine the oil with the crude material from a previous identical preparation (beginning with 30.2 g of amide starting material). Pass the oil through a silica gel plug eluting with methylene chloride to remove a higher Rf component. Elute with 1% methanol in dichloromethane and concentrate to obtain a solid (57.8 g). Suspend the solid in ether (1 L) and allow to stand overnight. Collect the solid by filtration and wash with a small amount of ether to obtain 47.5 g. Concentrate the filtrate, suspend in ether (100 mL) and allow to stand at room temperature for 2 h. Collect an additional 3.1 g of desired product by filtration. Concentrate the filtrate and purify the residue by silica plug filtration to obtain an additional 2.9 g of an orange solid. Combine all solids to obtain the title compound (53.5 g, 89%). $[\alpha]D^{20}$–36 (c=1.0 in DMSO). $^1$H NMR (400 MHz, DMSO-$d_6$) δ 1.21 (m, 1H), 2.06 (m, 1H), 2.18 (m, 1H), 2.42 (m, 2H), 2.87 (d, 1H), 2.95 (d, 1H), 3.18 (t, 1H), 3.42 (t, 1H), 3.73 (d, 1H), 3.85 (d, 1H), 4.19 (m, 1H), 7.03 (d, 1H), 7.66 (dd, 1H), 8.01 (d, 1H), 8.18 (s, 1H). LC-MS m/z 342.0, 344.0 (1:1 isotope ratio) [M+H]$^+$.

PREPARATION 16

(E)-[4-(3-Fluoro-6H-dibenzo[b,e]oxepin-11-ylidenemethyl)-2-nitro-phenyl]-((7R, 8aR)-hexahydro-pyrrolo[2,1-c][1,4]oxazin-7-yl)-amine

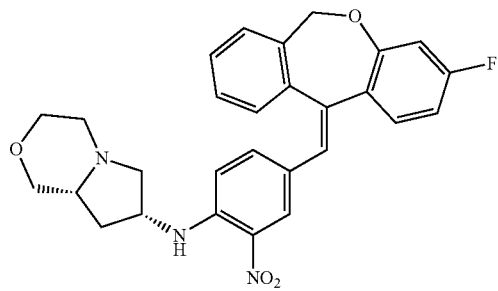 [SMILES: O=[N+]([O-])c1cc(/C=C2\c3ccccc3COc3cc(F)ccc32)ccc1N[C@@H]1C[C@@H]2COCCN2C1]

Charge a flask with (7R,8aR)-(4-bromo-2-nitro-phenyl)-(hexahydro-pyrrolo[2,1-c][1,4]oxazin-7-yl)-amine (50.9 g, 0.149 mol), (E)-2-((3-fluorodibenzo[b,e]oxepin-11(6H)-ylidene)methyl)-4,4,5,5-tetramethyl-1,3,2-dioxaborolane (57.5 g, 0.163 mol), triphenylphosphine (10.1 g, 39 mmol) and sodium methoxide (19.7 g, 0.346 mol) in tetrahydrofuran (1 L) and methanol (500 mL). Bubble nitrogen through the mixture for 30 min. Add palladium (II) acetate (3.00 g, 13 mmol) and bubble nitrogen through the mixture for an additional 30 min. Heat at reflux (60° C.) under nitrogen for 16 h. Cool to room temperature, filter through diatomaceous earth and concentrate in vacuo to obtain a solid. Dissolve in 1:1 ethyl acetate/brine (2 L) and pass through a pad of diatomaceous earth. Wash the pad with 1:1 ethyl acetate/brine (2×1 L) and then with 10% methanol in dichloromethane (4×1 L). Separate the layers and combine the organic phases. Dry the organic portion over sodium sulfate, filter, and concentrate to obtain an oil. Dissolve the oil in dichloromethane and pass through an silica gel pad. Rinse the pad with dichloromethane until higher Rf TLC component is removed. Elute with 1% methanol in dichloromethane and concentrate in vacuo to obtain a foam. Dissolve in ethyl acetate (2 L) and concentrate to approximately 200 mL. Add hexanes (1.5 L) and allow the suspension to stand at room temperature for one hour. Collect the orange solid by filtration and dry at 50° C./20 mm Hg to obtain the title compound (53 g, 73%). $[\alpha]_D^{20}$–26 (c=1.0 in DMSO). $^1$H NMR (400 MHz, DMSO-$d_6$) δ 1.08 (m, 1H), 2.02 (m, 1H), 2.17 (m, 1H), 2.41 (m, 2H), 2.88 (m, 1H), 3.17 (m, 1H), 3.40 (m, 1H), 3.73 (d, 1H), 3.82 (d, 1H), 4.12 (m, 1H), 5.02 (broad s, 1H), 5.59 (broad s, 1H), 6.60 (d, 1H), 6.81 (m, 2H), 6.96 (s, 1H), 7.05 (m, 2H), 7.28 (t, 1H), 7.38 (t, 1H), 7.60 (m, 2H), 7.84 (s, 1H), 8.05 (d, 1H). LC-MS m/z 458.3 [M+H]$^+$.

EXAMPLE 1

5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one
(Form I)

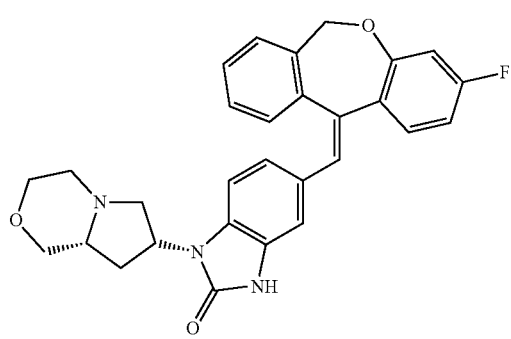

Hydrogenate a mixture of (E)-[4-(3-fluoro-6H-dibenzo[b,e]oxepin-11-ylidenemethyl)-2-nitro-phenyl]-((7R,8aR)-hexahydro-pyrrolo[2,1-c][1,4]oxazin-7-yl)-amine (52 g, 0.107 mol), triethylamine (33 mL, 0.237 mol) and 5% platinum on carbon (18 g) in tetrahydrofuran (450 mL) at room temperature at 50 psi for 2 h. Filter off the catalyst, rinse with tetrahydrofuran, and concentrate to obtain a brown foam. Dissolve the foam in anhydrous tetrahydrofuran (500 mL) and cool in an ice bath. Add triphosgene (31.5 g, 0.106 mol) in tetrahydrofuran (450 mL) dropwise over 30 min and stir at room temperature for 16 h. Concentrate the solution, dissolve in 5% methanol in dichloromethane and purify through a short silica gel plug. Concentrate to obtain a brown solid. Suspend the solid in saturated sodium bicarbonate (1.5 L) and stir on the rotary evaporator for one hour. Filter and dry in vacuo. Dissolve in warm 1:1 methanol/dichloromethane (approximately 6 L) and treat with poly (4-vinylpyridine) 2% cross-linked resin (170 g). Stir the slurry for 30 min and filter through diatomaceous earth. Concentrate the filtrate to approximately 1.5 L volume and collect the resulting solids by filtration. Dry at 80° C./20 mm Hg overnight to obtain the title compound as a white solid (38.1 g, 74%). $[\alpha]D^{20}$–20.5 (c=1.0 in DMSO). $^1$H NMR (400 MHz, DMSO-$d_6$) δ 1.48 (m, 1H), 2.02 (m, 1H), 2.19 (m, 2H), 2.52 (m, 1H), 2.91 (d, 1H), 3.03 (d, 1H), 3.25 (t, 1H), 3.50 (t, 1H), 3.79 (d, 1H), 3.88 (d, 1H), 4.95 (m, 1H), 5.03 (broad s, 1H), 5.60 (broad s, 1H), 6.59 (m, 2H), 6.78 (m, 2H), 6.97 (s, 1H), 7.02 (d, 1H), 7.25 (t, 1H), 7.38 (t, 1H), 7.48-7.61 (m, 3H), 10.72 (s, 1H, NH). LC-MS m/z 484.0 [M+H]$^+$.

Using material prepared as described in Example 1, X-ray powder diffraction patterns are obtained and reveal a crystal form (Form I) having characteristic peak positions (°2θ values) of about 10.5, 13.0, 15.5, and 19.7. The melting point characteristics of the material are determined by DSC. Onset melt=298.9° C.

EXAMPLE 1(A)

5-((E)-(3-fluorodibenzo[b,e]oxepin-11(6H)-ylidene) methyl)-1-((7R,8aR)-hexahydro-1H-pyrrolo[2,1-c] [1,4]oxazin-7-yl)-1H-benzo[d]imidazol-2(3H)-one (Form II)

Add 117.7 mg of 5-((E)-(3-fluorodibenzo[b,e]oxepin-11 (6H)-ylidene)methyl)-1-((7R,8aR)-hexahydro-1H-pyrrolo [2,1-c][1,4]oxazin-7-yl)-1H-benzo[d]imidazol-2(3H)-one (prepared as described in Example 1) into a vial and mix with 2.5 mL of DMAC on a stirplate at 1000 rpm and 70° C. until dissolved. Add water to the sample slowly until cloudy then remove heat. Continue to stir for 30 minutes until a white solid precipitates from solution. Collect the solids by filtration and dry overnight at 40° C.

Using material prepared as described in Example 1(a), X-ray powder diffraction patterns are obtained and reveal a crystal form (Form II) having characteristic peak positions (°2θ values) of about 11.3, 12.1, 18.8, and 21.0.

Alternate Procedures:

(i) Extract a suspension of 5-((E)-(3-fluorodibenzo[b,e] oxepin-11(6H)-ylidene)methyl)-1-((7R,8aR)-hexahydro-1H-pyrrolo[2,1-c][1,4]oxazin-7-yl)-1H-benzo[d]imidazol-2 (3H)-one.4-methylbenzenesulfonate (10.2 g, 15.55 mmoles) (prepared essentially as described in Example 2 below) in 1 N NaOH (200 mL) with 5% MeOH/CHCl$_3$ solution (5×100 mL) in a separatory funnel Wash the organic layer with brine, dry over sodium sulfate, filter through a pleated filter, and concentrate in vacuo. Dry the residue in 50° C. vacuum oven overnight to obtain white solid (6.71 g, 90% recovery). LC-MS (4 min): RT=1.87 min., 100% M+H=484.2.

(ii) Treat a 0.1 g sample of material from alternate procedure (i), above, with 1 mL DMAc and heat the resulting suspension in a 80° C. oil bath for 30 min. Add 15 mL of AcCN to the solution, heat in a 80° C. oil bath for 30 min, then cool to room temperature with stirring. Solids are collected by filtration then dried in 50° C. vacuum oven overnight to recover 74.5 mg of product.

(iii) Treat a 0.1 g sample of material from alternate procedure (i), above, with 20 mL AcCN and heat the resulting suspension in a 80° C. oil bath for 30 min., then cool to room temperature with stirring. Solids are collected by filtration then dried in 50° C. vacuum oven overnight to recover 81.8 mg of product.

(iv) Treat a 0.1 g of sample of material from alternate procedure (i), above, with 20 mL IPA and heat the resulting suspension in a 80° C. oil bath for 30 min., then cool to room temperature with stirring. Solids are collected by filtration then dried in 50° C. vacuum oven overnight to recover 92.8 mg of product.

Using material prepared as described in Alternate procedure (i), above, X-ray powder diffraction reveals a crystal form having characteristic peak positions (°2θ values) of about 11.3, 12.1, 18.8, and 21.0 (Form II).

EXAMPLE 2

5-((E)-(3-fluorodibenzo[b,e]oxepin-11(6H)-ylidene) methyl)-1-((7R,8aR)-hexahydro-1H-pyrrolo[2,1-c] [1,4]oxazin-7-yl)-1H-benzo[d]imidazol-2(3H)-one. tosylate salt

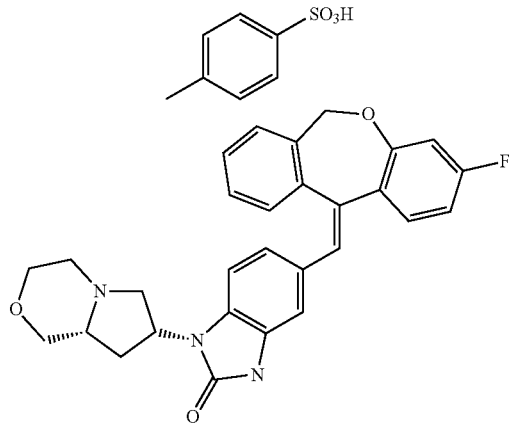

Heat a solution of p-toluenesulfonic acid monohydrate (51.70 mmol, 9.98 g) in dimethylacetamide (50 mL) in a 40° C. oil bath for 30 minutes. To the homogeneous solution add 5-((E)-(3-fluorodibenzo[b,e]oxepin-11(6H)-ylidene)methyl)-147R,8aR)-hexahydro-1H-pyrrolo[2,1-c][1,4]oxazin-7-yl)-1H-benzo[d]imidazol-2(3H)-one (51.70 mmol, 25.00 g) in 5 g portions with vigorous stirring. Wash the powder funnel and container bottle with dimethylacetamide (25 mL) and stir the suspension at 40° C. for 30 minutes until the solid dissolves completely. Place the light brown homogeneous solution in a stream of nitrogen gas overnight at 30° C. Dilute the residue with acetonitrile (200 mL) and sonicate in a water bath for 20 minutes. Heat the white solid suspension in a 60° C. oil bath for 3 hours. Cool to room temperature and collect the solid by filtration. Dry in a vacuum oven at 40° C. for 2 days to obtain the title compound (32.88 g, 97%). $^1$H NMR (400 MHz, DMSO-d$_6$) δ 2.00 (m, 0.5H), 2.29 (m, 0.5H), 2.44 (s, 3H), 2.48 (m, 0.5H), 3.1-4.2 (m, 7H), 5.10 (broad m, 2H), 5.55 (broad s, 1H), 6.60 (dd, 1H), 6.67 (d, 1H), 6.78 (m, 2H), 6.95 (m, 3H), 7.08 (d, 2H), 7.21 (t, 1H), 7.33 (t, 1H), 7.43 (d, 2H), 7.57 (m, 2H), 9.65 (s, 0.5H), 10.25 (s, 0.5H), 10.98 (s, 0.5H), 11.14 (s, 0.5H). LC-MS m/z 484.2 [M+H]$^+$.

Alternate Procedures:

(a) Dissolve 85.8 mg (0.177 mmol) of 5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one (prepared essentially as described in Example 1) in dimethyl acetamide (2 mL). Add p-toluenesulfonic acid monohydrate (43 mg, 0.226 mmol) and stir until the mixture is a clear solution. Add acetonitrile (7 mL) and evaporate to obtain a clear oil. Add water (2 mL) and sonicate the sample. After a white solid precipitates, slurry the sample for 10 min. Filter and dry to obtain a solid.

(b) Dissolve 98.0 mg of 5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2 (3H)-one (prepared essentially as described in Example 1) in 2.5 mL of DMAC. Add 1.2 eq. of p-toluenesulfonic acid monohydrate and stir until solution is clear and colorless. Add 2 mL of 88% acetone then 16 mL of water then evaporate to remove solvents. To the resulting clear oil, add 1 mL of acetone and sonicate. Dry the resulting gel to obtain an off-white solid. Dissolve the solid again in 1:10 THF:H2O and evaporate to obtain a clear oil then sonicate with 5 mL of acetonitrile. After a white solid precipitates, slurry the sample overnight. Filter and dry to obtain a solid.

What is claimed is:

1. A compound which is 5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one, or a pharmaceutically acceptable salt thereof.

2. A compound according to claim 1 which is 5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one.

3. The compound according to claim 2 in crystalline form.

4. The compound according to claim 2 in crystalline form having characteristic peaks at 2θ of about 11.3, 12.1, 18.8, and 21.0.

5. A method of treating congestive heart failure, hypertension, diabetic nephropathy, or chronic kidney disease, comprising administering to a patient in need thereof an effective amount of a compound or salt according claim 1.

6. A pharmaceutical composition comprising a compound or salt according to claim 1 in combination with one or more pharmaceutically acceptable carriers, diluents, or excipients.

7. The pharmaceutical composition according to claim 6 comprising 5-((E)-(3-fluorodibenzo[b,e]oxepin-11(6H)-ylidene)methyl)-1-((7R,8aR)-hexahydro-1H-pyrrolo[2,1-c][1,4]oxazin-7-yl)-1H-benzo[d]imidazol-2(3H)-one in combination with one or more pharmaceutically acceptable carriers, diluents, or excipients.

* * * * *

UNITED STATES PATENT AND TRADEMARK OFFICE
CERTIFICATE OF CORRECTION

PATENT NO.       : 8,658,638 B2
APPLICATION NO.  : 13/203518
DATED            : February 25, 2014
INVENTOR(S)      : David Andrew Coates et al.

It is certified that error appears in the above-identified patent and that said Letters Patent is hereby corrected as shown below:

Delete Title page and replace with new Title Page. (attached)

In the Specification

On the first page, Column 2, lines 2-3, please delete

"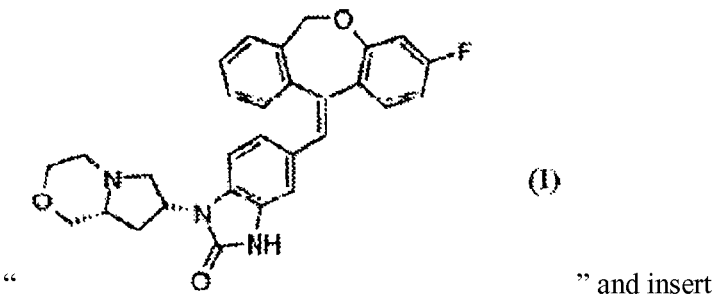" and insert

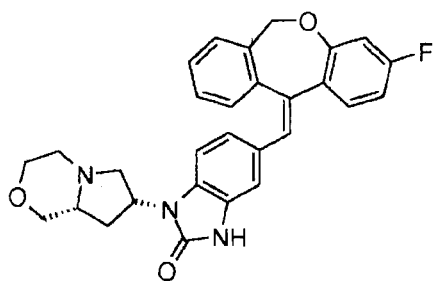
-- Compound (I)                         --, therefor.

In the Claims

In column 24, line 8, in Claim 5, please delete "according" and insert --according to--, therefor.

Signed and Sealed this
Seventeenth Day of June, 2014

Michelle K. Lee
*Deputy Director of the United States Patent and Trademark Office*

(12) United States Patent
Coates et al.

(10) Patent No.: US 8,658,638 B2
(45) Date of Patent: Feb. 25, 2014

(54) MINERALOCORTICOID RECEPTOR ANTAGONIST AND METHODS OF USE

(75) Inventors: David Andrew Coates, Indianapolis, IN (US); Konstantinos Gavardinas, Monrovia, IN (US); Prabhakar Kondaji Jadhav, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 94 days.

(21) Appl. No.: 13/203,518

(22) PCT Filed: Mar. 4, 2010

(86) PCT No.: PCT/US2010/026138
§ 371 (c)(1),
(2), (4) Date: Aug. 26, 2011

(87) PCT Pub. No.: WO2010/104721
PCT Pub. Date: Sep. 16, 2010

(65) Prior Publication Data
US 2011/0312954 A1  Dec. 22, 2011

Related U.S. Application Data

(60) Provisional application No. 61/159,578, filed on Mar. 12, 2009.

(51) Int. Cl.
*C07D 498/04* (2006.01)
*A61K 31/5365* (2006.01)

(52) U.S. Cl.
USPC .................................. 514/230.5; 544/105

(58) Field of Classification Search
USPC .................................. 544/105; 514/230.5
See application file for complete search history.

(56) References Cited

FOREIGN PATENT DOCUMENTS

| WO | 2004052847 | 6/2004 |
|----|------------|--------|
| WO | 2005066161 | 7/2005 |
| WO | 2009085584 | 7/2009 |

*Primary Examiner* — Kahsay Habte
(74) *Attorney, Agent, or Firm* — Elizabeth Dingess-Hammond; Alexander Wilson

(57) ABSTRACT

The present invention provides a compound of the formula:

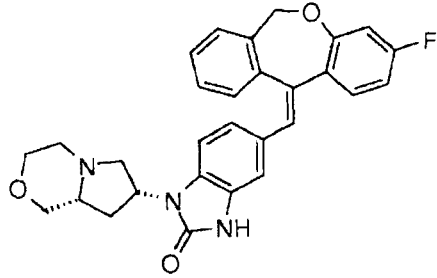

Compound (I)

or a pharmaceutically acceptable salt thereof; pharmaceutical compositions comprising Compound (I) in combination with a suitable carrier, diluent, or excipient; and methods for treating physiological disorders, particularly congestive heart failure, hypertension, diabetic nephropathy, or chronic kidney disease, comprising administering Compound (I), or a pharmaceutically acceptable salt thereof.

7 Claims, No Drawings